US008097236B2

(12) United States Patent
Aston et al.

(10) Patent No.: US 8,097,236 B2
(45) Date of Patent: Jan. 17, 2012

(54) DEVICES AND METHODS FOR THE TREATMENT OF CANCER

(75) Inventors: Roger Aston, Malvern (GB); Leigh T Canham, Malvern (GB)

(73) Assignee: pSiMedica Limited, Worcestershire (GB)

(*) Notice: Subject to any disclaimer, the term of this patent is extended or adjusted under 35 U.S.C. 154(b) by 182 days.

(21) Appl. No.: 10/468,742

(22) PCT Filed: Feb. 20, 2002

(86) PCT No.: PCT/GB02/00721
§ 371 (c)(1), (2), (4) Date: Aug. 22, 2003

(87) PCT Pub. No.: WO02/067998
PCT Pub. Date: Sep. 6, 2002

(65) Prior Publication Data
US 2004/0091421 A1    May 13, 2004

(30) Foreign Application Priority Data

Feb. 22, 2001   (GB) .................................. 0104383.5

(51) Int. Cl.
*A61K 51/00* (2006.01)
*A61M 36/14* (2006.01)
(52) U.S. Cl. ...................... 424/1.11; 424/1.33; 424/1.77
(58) Field of Classification Search .................. 424/1.11, 424/1.77
See application file for complete search history.

(56) References Cited

U.S. PATENT DOCUMENTS

| 4,994,013 | A | * | 2/1991 | Suthanthiran et al. ............ 600/8 |
| 5,256,765 | A | | 10/1993 | Leong |
| 5,582,172 | A | | 12/1996 | Papisov et al. |
| 5,609,629 | A | | 3/1997 | Fearnot et al. |
| 5,795,286 | A | | 8/1998 | Fischell et al. |
| 5,824,049 | A | | 10/1998 | Ragheb et al. |
| 5,873,904 | A | | 2/1999 | Ragheb et al. |
| 5,894,133 | A | * | 4/1999 | Armini ....................... 250/492.3 |
| 6,096,070 | A | | 8/2000 | Ragheb et al. |
| 6,241,962 | B1 | * | 6/2001 | Nicolini et al. .............. 424/1.61 |
| 6,248,057 | B1 | * | 6/2001 | Mavity et al. ..................... 600/3 |
| 6,322,895 | B1 | * | 11/2001 | Canham ........................ 428/450 |
| 6,352,682 | B2 | | 3/2002 | Leavitt et al. |
| 6,358,613 | B1 | | 3/2002 | Buriak |
| 6,379,648 | B1 | | 4/2002 | Day et al. |
| 6,575,888 | B2 | | 6/2003 | Zamora et al. |
| 6,676,595 | B1 | * | 1/2004 | Delfino ........................... 600/30 |
| 7,763,277 | B1 | * | 7/2010 | Canham et al. ............... 424/489 |
| 2001/0044567 | A1 | | 11/2001 | Zamora et al. |
| 2002/0055666 | A1 | | 5/2002 | Hunter et al. |
| 2004/0010313 | A1 | | 1/2004 | Aston et al. |

FOREIGN PATENT DOCUMENTS

| DE | 197 54 870 | 8/1998 |
| EP | 0 407 623 | 1/1991 |
| EP | 0407 623 | 1/1991 |
| JP | 59-101145 | 6/1984 |
| WO | WO 93/14787 | 8/1993 |
| WO | WO 94/02068 | 2/1994 |
| WO | WO 95 03036 | 2/1995 |
| WO | WO 96 25176 | 8/1996 |
| WO | WO 98/17331 A | 4/1998 |
| WO | WO 98 43618 | 10/1998 |
| WO | WO 98/59347 A | 12/1998 |
| WO | WO 99/37409 A | 7/1999 |
| WO | WO 99/39746 | 8/1999 |
| WO | WO 99/53898 A | 10/1999 |
| WO | WO 00/59550 A | 10/2000 |
| WO | WO/00/66190 | * 11/2000 |
| WO | WO 01/36007 A | 5/2001 |

OTHER PUBLICATIONS

Haas et al. (IEEE Transactions on Electron Devices 1976, 23, 803-805).*
Becker et al., "Phase I-II Study of Simultaneous Radiotherapy and Paclitaxel (Taxol) in a Twice a Week (TIW) Schedule for Recurrent Squamous Cell Carcinomas of the Head and Neck (SCCHN)," European Journal of Cancer, Pergamon Press, Oxford, GB, vol. 33, Sep. 1997, pp. S193.
Zanelli et al., "Paclitaxel as a Radiosensitiser: A Proposed Schedule of Administration Based on in Vitro Data and Pharmacokinetic Calculaitions," European Journal of Cancer, Pergamon Press, Oxford, GB, vol. 33, No. 3, Mar. 1997, pp. 486-492.
Formenti et al., Concurrent Paclitaxel and Radiation in Locally Advanced Breast Cancer,: European Journal of Cancer, Pergamon Press, Oxford, GB, vol. 34, Sep. 30, 1998, p. S12.
Li et al., "Potentiation of Ovarian OCA-1 Tumor Radioresponse by Poly (L-Glutamic Acid)-Paclitaxel Conjugate," Internal Journal of Radiation: Oncology Biology Physics, Pergamon Press, vol. 48, No. 4, Nov. 1, 2000, pp. 1119-1126.
Mote et al., "Paclitaxel Sensitizes Multidrug Resistant Cells to Radiation," Anti-Cancer Drugs, Oxford, GB, vol. 7, No. 2, Feb. 1, 1996, pp. 182-188.
Milas et al., "Enhancement of Tumore Radioresponse of a Murine by Paclitaxel," Cancer Research, American Association for Cancer Research, Baltimore, MD, vol. 54, 1994, pp. 3506-3510.
Kornowski et al., "Slow-release Taxol Coated GRII Stents Reduce Neointima Formation in a Porcine Coronary In-stent Restenosis Model," 70th Scientific Sessions of the American Heart Association, Orlando, Florida, Nov. 9-12, 1997, vol. 96, No. 8 Suppl., 1997, p. 1341.
Farb et al., "Pacilitaxel Polymer-coated Stents Reduce Neointima," 70th Scientific Sessions of the American Heart Association, Orlando, Florida, Nov. 9-12, 1997, vol. 96, No. 8 Suppl., p. 1608.
Haehnel et al., "Local Growth Inhibitory Effect of Paclitaxel Released by a Biodegradable Stent Coating on Vascular Smooth Muscle Cells," XIXth Congress of the European Society of Cardiology Together With the 32nd Annual General Meeting of the Association of European Paediatric, Stockholm, Sweden, Aug. 24-28, 1997, vol. 18, No. Abstr. Suppl., p. 460.

(Continued)

Primary Examiner — Michael G Hartley
Assistant Examiner — Melissa Perreira
(74) Attorney, Agent, or Firm — Nixon & Vanderhye PC

(57) ABSTRACT

The invention relates to the treatment of cancer. In particular the invention relates to an internal therapeutic product comprising: (i) an anti-cancer component selected from one or both of: a radionucleotide, a cytotoxic drug; and (ii) a silicon component selected from one or more of: resorbable silicon, biocompatible silicon, bioactive silicon, porous silicon, polycrystalline silicon, amorphous silicon, and bulk crystalline silicon, the internal therapeutic product being for the treatment of cancer.

5 Claims, No Drawings

OTHER PUBLICATIONS

Manifold et al., "Taxol Coated Stents in Oesophageal Adenocarcinoma," Digestive Disease Week and the 99th Annual Meeting of the American Gastroenterological Association, New Orleans, Louisiana, May 16-22, 1988, vol. 114, No. 4, Part 2, Apr. 15, 1998, p. A27.

Voisard et al., Paclitaxel-Coated Biodegradable Stents Inhibit Proliferative Activity and Severely Damage Cyoskeletal Components of Smooth Muscle Cells From Human Coronary Plaque Material in Vitro, XXth Congress of the European Society of Cardiology, Vienna, Austria, Aug. 22-26, 1998, vol. 19, No. Abst. Suppl., Aug. 1998, p. 376.

Haehnel et al., "Differential Effect of a Local Paclitaxel Release From a Biodegradable Stent Coating on Vascular Smooth Muscle Cells and Endothelial Cells in a Coculture Model," 48th Annual Scientific Session of the American College of Cardiology, New Orleans, Louisiana, Mar. 7-10, 1999, vol. 33, No. 2 Suppl. A, Feb. 1999, p. 222A.

Canham et al, "Will a Chip Every Day Keep the Doctor Away?", Physics World (2001), 14(7), Jul. 27-31, 2001; XP008010482.

Coffer et al, "Fabrication and Characterization of Calcium Phosphate/Porous Silicon/Silicon Structures Doped with Platinum Antitumor Compounds", Materials Research Society Symposium Proceedings (2000), 599 (Mineralization in Natural and Synthetic Biomaterials), 61-65, 2000, XP008010745.

* cited by examiner

DEVICES AND METHODS FOR THE TREATMENT OF CANCER

This application is the U.S. national phase of international application PCT/GB02/00721, filed Feb. 20, 2002, which designated the U.S.

This invention relates to devices and methods for treatment of cancer, including liver cancer, kidney cancer, prostate cancer, brain cancer, and breast cancer. More specifically the invention relates to devices and methods or the treatment of liver cancer.

Liver cancer is characterised by the growth of one or more tumours in the lobes of the liver. Only 5% of liver cancers can be treated by surgery. These tumours may arise directly from the liver tissue or from metastasis from tumours in another part of the body. Metastasis of cancer to the liver is a common cause of death for cancer patients.

Primary liver cancer is one of the most common cancers in the world. The greatest incidence of this disease is in Asian states where hepatitis is prevalent. The two principal causes of primary liver cancer are hepatitis B and excessive alcohol consumption.

Radiotherapy glasses have been used in the treatment of liver cancer with beta or gamma radiation. Glasses that have been employed are biocompatible and substantially insoluble in the body of the patient. Insolubility is considered to be an important factor, since it prevents unwanted release of the radioisotope from the target site.

An example of a radiotherapy glass, used in the treatment of liver cancer, is yttrium aluminosilicate. This has been administered to the liver by injection of microparticles comprising the glass, into the hepatic artery which is the primary blood supply for target tumours. The size of the microparticles is such that the blood carries them into the capillary bed of the liver, but they are too large to pass completely through the liver and into the circulatory system. The microparticles follow the flow of blood to the tumour, which has a greater than normal blood supply. The patient may benefit from a combined treatment of the liver with the microparticles together with perfusion of cytotoxic drugs into the arterial circulation of the liver.

Unfortunately the requirement that the radioactive glass should be insoluble may impair treatment of the cancer: The continued presence of cancer after the isotope has decayed, may mean that further treatment using glass microparticles would be desirable. However, the presence of the, now non-radioactive, particles around the cancer reduces the effectiveness of further treatment with radioactive particles.

A further problem, applicable to other forms of cancer treatment involving the use of implantation, is the interference of the implant with monitoring of the tumour.

When microparticles are administered into the arterial blood supply of the liver, it is advantageous for them to have a size, shape, and density that results in a relatively homogeneous distribution within the liver. If uniform distribution does not occur, then they may cause excessive radiation in the areas of highest concentration, There are therefore a number of factors that influence the effectiveness of treatment using radioactive microparticles. These factors include particle size, solubility, biocompatability, stability to radiation, density, and shape.

The use of microparticles for the treatment of liver cancer forms part of a larger field of cancer treatment in which implants are used to deliver radiation and chemotherapeutic agents. Cancers treatable in this way also include breast cancer, kidney cancer, prostate cancer, and brain cancer. For example radioactive seeds and pellets are presently used in brachytherapy of tumours, a form of therapy that involves the implantation of a radiation source to provide localised treatment of the tumour. Brachytherapy contrasts with other methods of treatment that involve treatment of a site with a radiation source that is external to the patient's body.

It is an objective of this invention to address at least some of the above mentioned problems.

According to a first aspect, the invention provides an internal therapeutic product comprising:
(i) an anti-cancer component comprising at least one radionucleotide and/or at least one cytotoxic drug; and
(ii) a silicon component selected from one or more of: resorbable silicon, biocompatible silicon, bioactive silicon, porous silicon, polycrystalline silicon, amorphous silicon, and bulk crystalline silicon.

For the purposes of this specification bioactive silicon is silicon that is capable of forming a bond with tissue of a patient, resorbable silicon is silicon that is capable of resorbing in body fluid of a patient, and biocompatible silicon is silicon that is biocompatible for the purposes of anti-cancer treatment. Certain forms of porous and polycrystalline silicon have been found to be bioactive and/or resorbable, as disclosed in PCT/GB96/01863.

For the purposes of this specification a radionucleotide is to be taken as a radioactive nuclide. Radionucleotides are also commonly referred to as radionuclides.

The therapeutic product may comprise at least one implant. The silicon component may comprise at least one implant. The or at least one of the implants may comprise a microparticle. The therapeutic product may comprise a suspension, suitable for injection into a patient, comprising the or at least one of the microparticles. The suspension may comprise an isotonic solution.

The or at least one of the implants may comprise one or more of the following: a seed, a pellet, a bead. The therapeutic product may comprise one or more of the following: a staple, a suture, a pin, a plate, a screw, a barb, coil, thread, and a nail.

The anti-cancer component may be selected from one or both of a radionucleotide, a cytotoxic drug.

Preferably the or at least one of the implants comprises silicon and has a shape and composition such that the or at least one of the implants is suitable for brachytherapy.

The use of silicon in the preparation of a therapeutic product for the treatment of cancer is advantageous because silicon may readily be processed by standard microfabrication techniques, to form articles such as staples, sutures, pins, plates, screws, barbs, and nails. Silicon in the form of porous silicon may also be transmuted into radioactive compositions, the nature of the transmutation being dependent upon the cancer to be treated.

The or at least one of the implants may comprise at least part of the silicon component and at least part of the anti-cancer component. The or at least one of the microparticles may comprise at least part of the silicon component and at least part of the anti-cancer component. The therapeutic product may comprise a multiplicity of silicon implants.

For example the internal therapeutic product may comprise a multiplicity of microparticles, each microparticle comprising porous silicon.

Preferably the largest dimension of the or at least one of the microparticles is in the range 0.1 to 100 μm. More preferably the largest dimension of the or at least one of the microparticles is in the range 20 to 50 μm.

If the internal therapeutic product is to be used for the treatment of liver cancer, and is to be delivered by injecting a suspension of microparticles into the hepatic artery, then the dimensions of at least some of the Microparticles must be such that they enter, but do not exit, the liver.

Preferably the largest dimension of the or at least one of the implants is in the range 0.01 mm to 30 mm. More preferably the largest dimension of the or at least one of the implants is in the range 0.5 mm to 30 mm. Yet more preferably the largest dimension of the or at least one of the implants is in the range 1 mm to 30 mm.

The largest dimension of at least one of the implants may be in the range 0.1 mm to 5 mm.

The implant may be introduced into any part of the patient's body in which a malignant tumour is located. For example the form of implant introduction may be subcutaneous, intramuscular, intraperitoneal, or epidermal. The implant may be implanted into an organ such as a liver, a lung, or a kidney. Alternatively the implant may be introduced into tissue consisting of vasculature or a duct.

Advantageously the specific gravity of the or at least one of the implants is between 0.75 and 2.5 g cm$^{-3}$, more advantageously the specific gravity of the or at least one of the implants is between 1.8 and 2.2 gcm$^{-3}$.

The use of porous silicon is advantageous in relation to the treatment of liver cancer. This is because the density of porous silicon may be controlled by altering its porosity. Particle density is an important factor in determining the success of treatment of liver cancer by administration of microparticles to the hepatic artery.

Preferably the silicon component comprises resorbable silicon. More preferably the silicon component comprises resorbable silicon and the anti-cancer component comprises a radionucleotide, the radionucleotide being distributed through at least part of the resorbable silicon. Yet more preferably the structure of the resorbable silicon is such that the half life of the radionucleotide is less than the time taken for resorbable silicon to substantially corrode when introduced into the patient. Even more preferably the structure of the resorbable silicon is such that the half life of the radionucleotide is less than one tenth the time taken for resorbable silicon to substantially corrode when introduced into the patient.

Advantageously the or at least one of the implants comprises resorbable silicon. More advantageously the or at least one of the implants comprises resorbable porous silicon.

The or at least one of the implants may comprise resorbable silicon and a radionucleotide, the resorbable silicon having a structure and composition such that substantially all the radionucleotide remains in and/or on at least part of the or at least one of the implants for a period, measured from the time of implantation, greater than the half life of the radionucleotide.

The or at least one of the implants may comprise resorbable silicon and a radionucleotide, the resorbable silicon having a structure and composition such that substantially all the radionucleotide remains in and/or on at least part of the or at least one of the implants for a period, measured from the time of implantation, greater than twice the half life of the radionucleotide.

The or at least one of the implants may comprise resorbable silicon and a radionucleotide, the resorbable silicon having a structure and composition such that substantially all the radionucleotide remains in and/or on at least part of the or at least one of the implants for a period, measured from the time of implantation, greater than ten times the half life of the radionucleotide.

By ensuring that the half life of the radionucleotide is less than the time taken for the resorbable silicon to corrode to any significant extent, for example when it is introduced to the liver of a patient, the danger of the radionucleotide escaping to other parts of the patient is reduced. In this way the implant may localise the radionucleotide to region of the tumour until the radioactivity has decayed to a safe level. The use of resorbable silicon ensures that repeated administration of the therapeutic product is effective. Once the radionucleotide has decayed, or cytotoxic drug has been delivered, the therapeutic product dissolves allowing a further dose of implants (for example microparticles) to be delivered to the region of the tumour.

The dissolution of the implant or implants as result of the use of resorbable silicon also may assist in the diagnostic imaging of the patient, since the tumour will not be masked once dissolution has occurred. Silicon contrasts with other resorbable materials such as polymers, in that it is highly stable to beta and gamma radiation used to treat liver cancer.

The silicon component may be micromachined to fabricate one or more implants having a predetermined size and shape, the size and/or shape being chosen to minimise trauma and/or swelling and/or movement of the implant.

Advantageously the silicon component comprises porous silicon. More advantageously the silicon component comprises porous silicon and the anti-cancer component comprises a cytotoxic drug, the cytotoxic drug being disposed in at least one of the pores of the porous silicon.

The or at least one of the implants may comprise resorbable silicon and a cytotoxic drug, the resorbable silicon having a structure and composition such that the implant remains sufficiently intact to substantially localise the drug release at the site of the implant.

The implant may be designed so that once the cytotoxic drug has been substantially completely released the implant is then resorbed, thereby allowing further implantation and/or diagnostic imaging of the patient.

Preferably the silicon component comprises resorbable silicon and porous silicon, a cytotoxic drug being disposed in at least one of the pores of the porous silicon and a radionucleotide being distributed through at least part of the resorbable silicon.

For example the internal therapeutic product may comprise some particles of resorbable silicon in which a radionucleotide has been introduced, and some particles of porous silicon into which a cytotoxic drug has been introduced. The internal therpeutic product may be fabricated by combining the two types of particles, immediately prior to administration to the patient. For example the two types of particles may be combined less than two hours prior to administration to the patient.

The resorbable silicon may comprise derivatised resorbable silicon. The porous silicon may comprise derivatised porous silicon, including the types of derivatised porous silicon disclosed in PCT/US99/01428 the contents of which are herein incorporated by reference.

For the purposes of this specification derivatised porous silicon is defined as porous silicon having a monomolecular, or monatomic layer that is chemically bonded to at least part of the surface, including the surface of the pores, of the porous silicon. The chemical bonding, between the layer and the silicon may comprise a Si—C and/or Si—O—C bonding.

The anti-cancer component may be covalently bonded to the surface of the silicon component. The silicon component may be porous silicon, the anti-cancer component may be a radionucleotide, and the radionucleotide may be covalently bonded to the surface of the porous silicon.

The use of porous and/or derivatised silicon is advantageous because the rate of resorption can be controlled by the appropriate choice of porosity and/or derivatisation of the silicon.

The anti-cancer component may comprise a cytotoxic drug, and the cytotoxic drug may be selected from one or more of an alkylating agent such as cyclophosphamide, a cytotoxic antibody such as doxorubicin, an antimetabolite such as fluorouracil, a vinca alkaloid such as vinblastine a hormonal regulator such as GNRH, and a platinum compound such as cis platin.

The anti-cancer component may comprise a radionucleotide, and the radionucleotide may be selected from one or more of $^{90}$Y, $^{32}$P, $^{124}$Sb, $^{114}$In, $^{59}$Fe, $^{76}$As, $^{140}$La, $^{47}$Ca, $^{103}$Pd, $^{89}$Sr, $^{131}$I, $^{125}$I, $^{60}$Co, $^{192}$Ir, $^{12}$B, $^{71}$Ge, $^{64}$Cu, $^{203}$Pb and $^{198}$Au.

The radionucleotide, such as $^{32}$P, may be an isotope having a structure and composition that is obtainable by the transmutation of $^{30}$Si. The radionucleotide, such as $^{32}$P, may be an isotope having a structure and composition that is obtainable by the transmutation of $^{30}$Si, the $^{30}$Si forming at least part of a sample of porous silicon. The radionucleotide, such as $^{32}$P, may be an isotope having a structure and composition that is obtainable neutron transmutation of $^{30}$Si, the $^{30}$Si forming at least part of a sample of porous silicon.

Preferably the internal therapeutic product comprises a porous structure, the porous structure comprising at least part of the silicon component and comprising a radionucleotide. More preferably the porous structure comprises a radionucleotide, the structure and composition of the radionucleotide being obtainable by the transmutation of $^{30}$Si atoms. Yet more preferably the internal therapeutic product comprises a porous structure, the porous structure comprising at least part of the silicon component and comprising a radionucleotide, the radionucleotide being $^{32}$P having a structure and composition obtainable by the transmutation of $^{30}$Si atoms.

The anti-cancer component may comprise a radionucleotide, such as $^{71}$Ge, having a structure and composition that is obtainable by the transmutation of $^{70}$Ge. The anti-cancer component may comprise a-radionucleotide, such as $^{71}$Ge, having a structure and composition that is obtainable by the neutron transmutation of $^{70}$Ge.

The anti-cancer component may comprise a radionucleotide, such as $^{71}$Ge, having a structure and composition that is obtainable by the transmutation of $^{70}$Ge atoms present in a silicon germanium alloy. The anti-cancer component may comprise radionucleotide, such as $^{71}$Ge, that is obtainable by the transmutation of $^{70}$Ge atoms present in a porous silicon germanium alloy.

The use of transmutation to fabricate the radionucleotide, from which the anti-cancer component is at least partly formed, may have several advantages. The distribution of the radionucleotide formed by transmutation, in an implant comprising porous silicon, may be substantially uniform. Such a uniform distribution should allow relatively high concentrations of the radionucleotide to be introduced into the porous silicon. Further, transmutation may allow the retention of a porous structure, and associated biological properties, of the silicon.

The anti-cancer component may comprise a radionucleotide and the silicon to component may comprise porous silicon. At least part of the radionucleotide may be distributed substantially uniformly through a cubic region of porous silicon having sides greater or equal to 0.1 microns. At least part of the radionucleotide may be distributed substantially uniformly through a cubic region of porous silicon having sides greater or equal to 1 micron. At least part of the radionucleotide may i be distributed substantially uniformly through a cubic region of porous silicon having sides greater or equal to 100 microns. At least part of the radionucleotide may be distributed substantially uniformly through a cubic region of porous silicon having sides greater or equal to 1000 microns.

According to a second aspect the invention provides a method of treating a cancer, the method comprising the step of introducing an internal therapeutic product into a patient, the internal therapeutic product comprising:
(i) a silicon component selected from one or more of resorbable silicon, biocompatible silicon, bioactive silicon, porous silicon, polycrystalline silicon, amorphous silicon, bulk crystalline silicon; and
(ii) an anti-cancer component comprising at least one radionucleotide and/or at least one cytotoxic drug.

Preferably the internal therapeutic product comprises an anti-cancer component selected from one or both of: a radionucleotide, a cytotoxic drug.

Advantageously the internal therapeutic product comprises at least one implant, the step of introducing the internal therapeutic product comprising the step of implanting the or at least one of the implants into the body of a patient. More advantageously the step of implanting the or at least one of the implants comprises the step of biolistically implanting the or at least one of the implants into organ(s) in which the cancer is located.

The step of implanting the or at least one of the implants may comprise the step of implanting the or at least one of the implants into one or more organs of the patient.

The or at least one of the implants may comprise at least part of the silicon component and at least part of the anti-cancer component The or at least one of the implants may comprise resorbable silicon and a cytotoxic drug, the method of treating a cancer comprising the further step of releasing at least part of the cytotoxic drug in such a manner that the release of the cytotoxic drug remains substantially localised to the point of implantation.

The or at least one of the implants may comprise resorbable silicon and a radionucleotide, the method of treating a cancer comprising the step of treating part of the patient's body with radiation from the radionucleotide in such a manner that the radiation treatment is localised to the point of implantation, and comprising the further step of allowing the silicon to substantially completely resorb once the half life of the radionucleotide has been exceeded.

The method of treating a cancer may be a method of brachytherapy.

Preferably the internal therapeutic product comprises a multiplicity of microparticles suspended in an isotonic solution, and the step of introducing the internal therapeutic product comprises the step of injecting the suspension into an artery or vein connected to and/or located in organ(s) in which the cancer is located.

At least one of said microparticles may comprise at least part of the silicon component and at least part of the anti-cancer component.

Preferably the method of treating cancer is a method of treating liver cancer and the step of introducing an internal therapeutic product comprises the step of introducing the therapeutic product into the liver of the patient.

Advantageously the internal therapeutic product comprises a radionucleotide and a cytotoxic drug and the method of treating cancer comprises the further step of combining the radionucleotide and the cytotoxic agent less than 10 hours prior the introduction of the therapeutic product to the patient. More advantageously the step of combining the nucleotide and the cytotoxic agent is performed less than 5 hours before the therapeutic product is introduced into the patient. Yet more advantageously the step of combining the nucleotide and the cytotoxic agent is performed less than 1 hour before the therapeutic product is introduced into the patient.

The cytotoxic drug may be selected from one or more of: an alkylating agent such as cyclophosphamide, a cytotoxic antibody such as doxorubicin, an antimetabolite such as fluorouracil, a vinca alkaloid such as vinblastine, a hormonal regulator such as GNRH, and a platinum compound such as cis plain.

The radionucleotide may be selected from one or more of $^{90}Y$, $^{32}P$, $^{124}Sb$, $^{114}In$, $^{59}Fe$ $^{76}As$, $^{140}La$, $^{47}Ca$, $^{103}Pd$, $^{89}Sr$, $^{131}I$, $^{125}I$, $^{60}Co$, $^{192}Ir$, $^{12}B$, $^{71}Ge$, $^{64}Cu$, $^{203}Pb$ and $^{198}Au$.

The radionucleotide, such as $^{32}P$, may be an isotope having a structure and composition that is obtainable by the transmutation of $^{30}Si$. The radionucleotide, such as $^{32}P$, may be an isotope having a structure and composition that is obtainable by the transmutation of $^{30}Si$, the $^{30}Si$ forming at least part of a sample of porous silicon. The radionucleotide, such as $^{32}P$, may be an isotope having a structure and composition that is obtainable neutron transmutation of $^{30}Si$, the $^{30}Si$ forming at least part of a sample of porous silicon.

Preferably the internal therapeutic product comprises a porous structure, the porous structure comprising at least part of the silicon component and comprising a radionucleotide. More preferably the porous structure comprises a radionucleotide, the structure and composition of the radionucleotide being obtainable by the transmutation of $^{30}Si$ atoms. Yet more preferably the internal therapeutic product comprises a porous structure, the porous structure comprising at least part of the silicon component and comprising a radionucleotide, the radionucleotide being $^{32}P$ having a structure and composition obtainable by the transmutation of $^{30}Si$ atoms.

The anti-cancer component may comprise a radionucleotide, such as $^{71}Ge$, having a structure and composition that is obtainable by the transmutation of $^{70}Ge$. The is anti-cancer component may comprise a radionucleotide, such as $^{71}Ge$, having a structure and composition that is obtainable by the neutron transmutation of $^{70}Ge$.

The anti-cancer component may comprise a radionucleotide, such as $^{71}Ge$, having a structure and composition that is obtainable by the transmutation of $^{70}Ge$ atoms present in a silicon germanium alloy. The anti-cancer component may comprise radionucleotide, such as $^{71}Ge$, that is obtainable by the transmutation of $^{70}Ge$ atoms present in a porous silicon germanium alloy.

According to a third aspect, the invention provides a use of an internal therapeutic product comprising:
(i) an anti-cancer component comprising at least one radionucleotide and/or at least one cytotoxic drug; and
(ii) a silicon component selected from one or more of: resorbable silicon, biocompatible silicon, bioactive silicon, porous silicon, polycrystalline silicon, bulk crystalline silicon, and amorphous silicon for the manufacture of a medicament for the treatment of cancer.

Advantageously the internal therapeutic product comprises an anti-cancer component selected from one or both of: a radionucleotide, a cytotoxic drug.

Preferably the use of an internal therapeutic product is for the manufacture of a medicament for the treatment of liver cancer.

Advantageously the use of an internal therapeutic product is for the manufacture of a medicament for the treatment of cancer by brachytherapy.

The therapeutic product may comprise at least one implant. The or at least one of the implants may comprise a microparticle. The therapeutic product may comprise a suspension, suitable for injection into a patent, comprising the or at least one of the microparticles. The suspension may comprise an isotonic solution.

The or at least one of the implants may comprise resorbable silicon and a cytotoxic drug, the resorbable silicon having a structure and composition such that the implant remains sufficiently intact to localise the drug release at the site of the implant.

The or at least one of the implants may comprise resorbable silicon and a radionucleotide, the resorbable silicon having a structure and composition such that substantially all the radionucleotide remains in and/or on at least part of the or at least one of the implants for a period, measured from the time of implantation, greater than the half life of the radionucleotide.

The or at least one of the implants may comprise resorbable silicon and a radionucleotide, the resorbable silicon having a structure and composition such that substantially all the radionucleotide remains in and/or on at least part of the or at least one of the implants for a period, measured from the time of implantation, greater than twice the half life of the radionucleotide.

The or at least one of the implants may comprise resorbable silicon and a radionucleotide, the resorbable silicon having a structure and composition such that substantially all the radionucleotide remains in and/or on at least part of the or at least one of the implants for a period, measured from the time of implantation, greater than ten times the half life of the radionucleotide.

Preferably the largest dimension of the or at least one of the implants is in the range 0.01 mm to 30 mm. More preferably the largest dimension of the or at least one of the implants is in the range 0.5 mm to 30 mm. Yet more preferably the largest dimension of the or at least one of the implants is in the range 1 mm to 30 mm.

The largest dimension of at least one of the implants may be in the range 0.1 mm to 5 mm.

The or at least one of the implants may comprise one or more of the following: a seed, a pellet, a bead. The therapeutic product may comprise one or more of the following: a staple, a suture, a pin, a plate, a screw, a barb, and a nail.

Preferably the or at least one of the implants comprises silicon and has a shape and composition such that the or at least one of the implants is suitable for brachytherapy.

The use of silicon in the preparation of a therapeutic product for the treatment of cancer is advantageous because silicon may readily be processed by standard microfabrication techniques, to form articles such as staples, sutures, pins, plates, screws, barbs, and nails.

The or at least one of the implants may comprise at least part of the silicon component and at least part of the anti-cancer component. The or at least one of the microparticles may comprise at least part of the silicon component and at least part of the anti-cancer component.

Preferably the largest dimension of the or at least one of the microparticles is in the range 0.1 to 100 μm. More preferably the largest dimension of the or at last one of the microparticles is in the range 20 to 50 μm.

The implant may be introduced into any part of the patient's body in which a malignant tumour is located. For example the form of implant introduction may be subcutaneous, intramuscular, intraperitoneal, or epidermal.

Advantageously the specific gravity of the or at least one of the implants is between 0.75 and 2.5 g $cm^{-3}$, more advantageously the specific gravity of the or at least one of the implants is between 1.8 and 2.2 $gcm^{-3}$.

Preferably the silicon component comprises resorbable silicon. More preferably the is silicon component comprises resorbable silicon and the anti-cancer component comprises a radionucleotide, the radionucleotide being distributed through at least part of the resorbable silicon. Yet more preferably the structure of the resorbable silicon is such that the half life of the radionucleotide is less than the time taken for resorbable silicon to substantially corrode when introduced into the liver of the patient. Even more preferably the structure of the resorbable silicon is such that the half life of the radionucleotide is less than one tenth the time taken for resorbable silicon to substantially corrode when introduced into the liver of the patient.

Preferably the silicon component comprises resorbable silicon and porous silicon, a cytotoxic drug being disposed in at least one of the pores of the porous silicon and a radionucleotide being distributed through at least part of the resorbable silicon.

The resorbable silicon may comprise derivatised resorbable silicon. The porous silicon may comprise derivatised porous silicon.

The cytotoxic drug may be selected from one or more of: an alkylating agent such as cyclophosphamide, a cytotoxic antibody such as doxorubicin, an antimetabolite such as fluorouracil, a vinca alkaloid such as vinblastine, a hormonal regulator such as GNRH, a platinum compound such as cis platin, and a radioactive agent.

The radionucleotide may be selected from one or more of: $^{90}$Y, $^{32}$P, $^{124}$Sb, $^{114}$In, $^{59}$Fe $^{76}$As, $^{140}$La, $^{47}$Ca, $^{103}$Pd, $^{89}$Sr, $^{131}$I, $^{125}$I, $^{60}$Co, $^{192}$Ir, $^{12}$B, $^{71}$Ge, $^{64}$Cu, $^{203}$Pb and $^{198}$Au.

For the purposes of this specification the term "patient" is either an animal patient or a human patient.

According to a fourth aspect the invention provides a radionucleotide having a structure and composition obtainable by the transmutation of $^{30}$Si, the $^{30}$Si forming at least part of a sample of porous silicon.

Preferably the readionucleotide has a structure and composition that is obtainable by neutron transmutation of $^{30}$Si, the $^{30}$Si forming at least part of a sample of porous silicon.

According to a fifth aspect the invention provides a radionucleotide, having a structure and composition obtainable by the transmutation of $^{30}$Si, for the treatment of cancer.

Preferably the radionucleotide has a structure and composition that is obtainable by neutron transmutation of $^{30}$Si.

Advantageously the radionucleotide has a structure and composition that is obtainable by transmutation of $^{30}$Si, the $^{30}$Si forming at least part of a sample of porous silicon. Advantageously the radionucleotide has a structure and composition that is obtainable by neutron transmutation of $^{30}$Si, the $^{30}$Si forming at least part of a sample of porous silicon.

The use of the radionucleotide may be for the treatment of liver cancer. The use of the radionucleotide may be for the treatment of cancer by brachytherapy.

According to a sixth aspect, the invention provides a method of fabricating a radionucleotide comprising the step of neutron transmuting $^{30}$Si, the $^{30}$Si forming at least part of a sample of porous silicon.

Preferably radionucleotide is $^{32}$P.

According to an seventh aspect, the invention provides a method of fabricating an internal therapeutic comprising the step (a) of transmuting silicon to form a radionucleotide.

Preferably radionucleotide is $^{32}$P.

Advantageously the silicon comprises $^{30}$Si.

Preferably the silicon is porous silicon.

Advantageously the method comprises the further step (b) of porosifying the silicon.

The step (b) may be performed after step (a). The step (b) may comprise the step of anodising silicon. The step (b) may comprise the step of stain etching silicon.

According to a eighth aspect, the invention provides a method of fabricating a radionucleotide comprising the step of neutron transmuting a porous silicon germanium alloy.

Preferably radionucleotide is $^{71}$Ge.

Advantageously the silicon germanium alloy comprises $^{70}$Ge.

According to a ninth aspect, the invention provides a method of fabricating an internal therapeutic comprising the step (a) of transmuting a silicon germanium alloy to form a radionucleotide.

Preferably radionucleotide is $^{71}$Ge.

Advantageously the step of transmuting the silicon germanium alloy comprises the step of transmuting $^{70}$Ge, the $^{70}$Ge forming at least part of the silicon germanium alloy.

Advantageously the method of fabricating an internal therapeutic product comprises the further step (b) of porosifying the silicon germanium alloy.

The step (b) may be performed after step (a). The step (b) may comprise the step of anodising silicon. The step (b) may comprise the step of stain etching silicon.

According to a further aspect, the invention provides an internal therapeutic product, as defined in any of the above aspects, for use as a medicament According to a yet further aspect the invention provides a use of an internal therapeutic product, as defined in any of the above aspects, for the manufacture of a medicament for the treatment of liver cancer. According to an even further aspect the invention provides a use of an internal therapeutic product, as defined in any of the above aspects, for the manufacture of a medicament for the treatment cancer by brachytherapy.

The invention will now be described by way of example only.

ADMINISTRATION OF THERAPEUTIC PRODUCTS, ACCORDING TO THE INVENTION, TO A PATIENT

Therapeutic products according to the present invention may have a variety of forms suitable for administration by subcutaneous, intramuscular, intraperitoneal, or epidermal techniques.

Therapeutic products according to the invention comprise a silicon component that may be spherical, lozenge shaped, rod shaped, in the form of a strip, or cylindrical. The silicon component may form part of or at least part of: a powder, a suspension, a colloid, an aggregate, and/or a flocculate. The therapeutic product may comprise an implant or a number of implants, the or each implant comprising silicon and an anti-cancer component. Such an implant or implants may be implanted into an organ in which a tumour is located in such a manner as to optimise the therapeutic effect of the anti-cancer component.

In one aspect of the invention, the method of treatment may involve brachytherapy, and the organ to undergo the brachytherapy may be surgically debulked and the residual space filled with the therapeutic product. In another aspect the organ to be treated may be cored with an array of needles and the cores back filled with the therapeutic product of the invention, such a procedure being suitable for brachytherapy of the prostate.

If the therapeutic product is to be used for the treatment of liver cancer, a composition may be administered to the liver by injection of silicon microparticles into the hepatic or celiac artery; the microparticles being delivered in the form of a suspension in an isotonic solution such as a phosphate buffered saline solution or serum/protein based solution. The size of the microparticles is such that the blood carries them into, but not out of, the liver. The microparticles follow the flow of blood to the tumour, which has a greater than normal blood supply.

In a yet further aspect, the therapeutic product may comprise a multiplicity of porous silicon particles, said multiplicity of porous silicon particles being divided into two types of porous silicon particles: one type having a cytotoxic drug and no radionucleotide, and a second type having a radionucleotide and no cytotoxic drug. Both types of particle may be administered to a patient at the same time, though they may be stored separately prior to administration. In this way the proportion of the cytotoxic drug and radionucleotide may be selected to correspond to the condition of the patient. Separate storage of the two types of microparticle prior to administration to a patient may be required if the cytotoxic agent is degraded by exposure to radiation from the radionucleotide.

To improve targeting further, a vasoconstricting drug such as angiotensin II may be infused prior to silicon microparticle administration. This drug constricts the fully developed non-tumour associated vasculature, and thereby directs the microparticles away from normal liver parenchyma.

Generation and/or Incorporation of the Radionucleotide

A therapeutic product according to the invention may comprise silicon component and a radionucleotide. The radionucleotide may be combined with the silicon component, and/or it may be fabricated by the transmutation of silicon. There are several methods by which a radionucleotide may be combined with a silicon component, or generated by the transmutation of silicon, to form the or at least part of a therapeutic product according to the invention. Four of these methods are given in sections (A) to (D) below.

(A) Fabrication of a $^{32}$P Dosed Porous Silicon Powder
Ai

A standard set of CZ Si wafers, degenerately doped with phosphorous ($2\times10^{20}$ cm$^{-3}$) is formed into a powder by ball milling, sieving, and wet etching. The milling and sieving is carried out in such a manner that silicon microparticles having a largest dimension in the range 25 to 50 μm are obtained. The powder is then rendered porous by stain etching in an HF based solution as described in Appl Phys Lett 64(13); 1693-1695 (1994) to yield porous silicon microparticles.

Alternatively a CZ Si wafer, degenerately doped with phosphorous ($2\times10^{20}$ cm$^{-3}$) wafer may be anodised in an HF solution, for example a 50% aqueous or ethanolic solution, to form a layer of porous silicon. The anodisation may be carried out in an electrochemical cell by standard methods such as that described in U.S. Pat. No. 5,348,618. For example a wafer may be exposed to an anodisation current density of between 5 and 500 mAcm$^{-2}$ for between 1 and 50 minutes. In this way a layer of porous silicon having a porosities in the range 1% to 90% may be fabricated.

The porous silicon layer may then be detached from the underlying bulk substrate by applying a sufficiently high current density in a relatively dilute electrolyte, for example a current density of greater than 50 mAcm$^{-2}$ for a period of 10 seconds. The detached porous silicon layer may then be crushed to yield porous silicon particles.

Attentively the anodised wafer may be treated ultrasonically to detach the layer of porous silicon and to break up the layer into particles of porous silicon. Exposure to ultrasound in this way may be performed in a solvent, the solvent being chosen to minimise agglomeration of the resulting particles. Ultrasonic treatment in this way results in the formation of porous silicon particles. Some control over particle sizes, of the porous silicon particles resulting from the ultrasonic treatment, may be achieved by centrifuging the resulting suspension to separate the different particle sizes. The porous silicon particles may also be sized by allowing the suspension to gradually settle as described in Phys. Solid State 36(8) 1294-1297 (1994).

Whether porosification is by stain etching or by anodisation, the porosity of the porous silicon may be selected so that the overall density of the microparticles for administration to the patient is between 1.5 and 2.5 g cm$^{-3}$. The density of the porous silicon may be tailored to take account of the density of the radionucleotide and or cytotoxic agent with which it is to be combined.

Silicon powders of micron particle size are available commercially and nanometer size particles can be fabricated by processes such as ball milling, sputtering, and laser ablation of bulk silicon.

Aii

A sample of porous silicon particles, fabricated according to step (Ai), are subjected to thermal neutron bombardment in a nuclear reactor to bring about neutron transmutation doping of the silicon. The irradiation conditions are chosen to maximise $^{32}$P production within the porous silicon. In this way 10-20 mCi levels may be obtained which are suitable for treatment of liver cancer tumours of 1 to 3 cm.

Phosphorous doping of silicon via neutron transmission doping of silicon is a well established means of producing phosphorous doped silicon at approximately $10^{15}$ cm$^{-3}$:

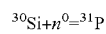

Further neutron capture is also possible:

The amount of $^{32}$P (a radionucleotide) present depends primarily on the amount of $^{31}$P produced and on the amount of P originally present, as well as the neutron flux.

If necessary, prior to the neutron radiation described in this section, concentrations of phosphorous in porosified particles could be raised by doping the porous silicon microparticles or particles with phosphine gas at 500 to 700 C or orthophosphoric acid followed by an anneal at 600 to 1000 C. Alternatively doping of the porous silicon microparticles or particles may be achieved by exposure to phosphorous oxychloride vapour at 800 to 900 C, as described in IEEE Electron Device Lett. 21(9), p 388-390 (2000). In this way concentrations of phosphorous between $10^{21}$ and $5\times10^{22}$ cm$^{-3}$ may be achieved.

(B) Isotope Exchange

Tritium gas is incubated with hydride passivated porous silicon. The hydride passivated porous silicon is irradiated with an electron beam in such a manner that the silicon—hydrogen bonds are progressively broken to allow replacement of the hydrogen with tritium. The electron beam may be a 1-10 MeV beam. The process results in the formation of tritiated porous silicon. A similar process of isotope exchange may also be used for the introduction of other radioactive gaseous species such as $^{131}$I that may become bonded to the internal surface of the pores. Isotope exchange may be promoted by the application of heat and/or light and/or particle bombardment.

(C) Ion Implantation

A sample of porous silicon may be oxidised by a low temperature oxidation process before ion implantation of the radionucleotide by standard techniques to fabricate a monolayer of oxide on the internal surface of the pores. The low temperature oxidation of the porous silicon being performed in such a manner that sintering of the porous silicon microstructure, by the ion implantation, is prevented. The low temperature oxidation may be performed by heating a sample of porous silicon at 300 C for 1 hour in substantially pure oxygen gas. The ion implantation may be performed in such a manner that ions of the radionucleotide are implanted between 1 and 5 microns below the surface of the porous silicon. Acceleration voltages for ion implantation may be in the range 5 KeV to 500 KeV and ion doses may be in the range $10^{13}$ to $10^{17}$ ion $cm^{-2}$. The temperature of the porous silicon may be maintained at a substantially fixed temperature during ion implantation. The temperature of the porous silicon may be in the range −200 C to +1000 C.

Examples of ions that may be ion implanted in this way are $^{90}Y$, $^{140}La$, $^{125}I$, $^{131}I$, $^{32}P$, and $^{103}Pd$.

(D) Liquid Infiltration

A sample of porous silicon is immersed in an aqueous solution of a salt of the radioisotope to be introduced. The salt is thermally decomposed by a first heat is treatment, and the radioisotope is driven into the skeleton of the porous silicon by a second heat treatment.

Alternatively if the salt of the radioisotope has a relatively low melting point the salt may be melted on the surface of the porous silicon, the molten salt being drawn into the porous silicon by capillary action. The salt may then be thermally decomposed and driven into the porous silicon skeleton by a two stage heating process as described in WO 99/53898.

(E) Fabrication of a Radionucleotide by Transmutation of a Silicon Germanium Alloy Ei A boron-doped polycrystalline silicon germanium bulk alloy may be grown by oriented crystallisation within a crucible using standard techniques such as the Polix method. The alloy may be fabricated in such a manner that the alloy comprises 1-15 at % Ge and has a resistivity of 1 to 0.01 ohm cm. The resulting ingot of the alloy may be mechanically sawn into sheets having thickness 200 to 500 microns, which may then be subjected to a wet polish etch to remove saw damage. Anodisation may then be performed at current densities in the range 5 to 500 $mAcm^{-2}$ in HF based electrolytes for periods between 5 minutes and 5 hours.

The resulting layer of porous Silicon germanium may then be converted to a powder of porous silicon germanium particles by similar methods to those described in section Ai.

The porous Silicon germanium powder may then be subjected to particle to bombardment, for example neutron bombardment, to transmute $^{70}Ge$ to the radionucleotide $^{71}Ge$.

Eii

Alternatively a standard Si or SOI wafer may be coated with a crystalline $Si_xGe_{(1-x)}$ layer, or with alternate ultrathin layers of crystalline silicon and germanium. The Si and Ge being fabricated from silane and germane by standard CVD techniques. The CVD deposition temperature may be in the range 300K to 1000K. For situations in which a silicon substrate is used porosification of the silicon germanium alloy may be by anodisation or by stain etching. For situations in which a SOI substrate is used, stain etching may be used to both porosify and detach the silicon alloy from the substrate.

Formation of the porous silicon alloy powder and transmutation is then performed in a similar manner as that described in (Ei).

Fabrication of Porous Silicon Implants Having a Well Defined Shape and Well Defined Dimensions A first Si wafer, having a sacrificial organic film applied to one surface, is etched using standard MEMS processing to form a first array of photolithographically defined objects. If the entire Si wafer thickness is etched through, then the first array is held in place by the sacrificial organic film. The first array is then bonded to a second electrically conductive wafer in preparation for subsequent anodisation. The second wafer may be silicon having the same conductivity type and different resistivity, or a metal coated silicon wafer having the same conductivity type and same resistivity as the first silicon wafer. The first array is then treated with solvent to remove the organic film. Anodisation in HF based electrolyte is then performed until the first array is completely porosified. Incorporation of the radioisotope may then be performed by treatment of the first array in powder form, or by treatment of the first array while bonded to the second wafer.

A similar process for the preparation of a second array of porous silicon photolithographically defined objects may also be performed by etching a SOI wafer by standard MEMS processing.

Combination of Silicon Microparticles with Cytotoxic Agent

The porous silicon microparticles, fabricated either by step (Ai) alone or by step (Ai) in combination with step (Aii), are then impregnated with a cytotoxic drug used for treating liver cancer, such as 5-fluorouracil.

There are a number of methods by which a cytotoxic drug may be associated with the microparticle. The cytotoxic drug may be dissolved or suspended in a suitable solvent, the microparticles may then be incubated in the resulting solution for a period of time. The cytotoxic drug may then be deposited on the surface of the microparticles. If the microparticles comprise porous silicon, then a solution of the cytotoxic drug may be introduced into the pores of the porous silicon by capillary action. Similarly if the microparticles have a cavity then the solution may also be introduced into the cavity by capillary action. If the cytotoxic drug is a solid but has a sufficiently high vapour pressure at 20 C then it may be sublimed onto the surface of the microparticles. If a solution or suspension of the cytotoxic drug can be formed then the substance may be applied to the microparticles by successive immersion in the solution/suspension followed by freeze drying.

A further method by which a cytotoxic drug may be associated with porous silicon is through the use of derivatised porous silicon. The cytotoxic drug may be covalently attached directly to the derivatised silicon by a Si—C or Si—O—C bond. The release of the cytotoxic agent is achieved through biodegradation of the porous silicon.

The invention claimed is:

1. A method of treating cancer by brachytherapy, the method comprising forming a therapeutic product which comprises non-derivatized porous silicon, doping the silicon with phosphorus, transmuting the phosphorus doped silicon to form a $^{32}P$ radionucleotide and implanting the therapeutic product into a tumor.

2. A method according to claim 1 wherein the therapeutic product comprises at least one microparticle, the microparticles having a size in the range 0.1 to 100 microns.

3. A method according to claim 2 wherein the microparticles have a size in the range 20 to 50 microns.

4. A method according to claim 1 wherein the method comprises implanting the therapeutic product into an organ.

5. A method according to claim 4 wherein the method comprises the step of implanting the therapeutic product into one or more of: a liver, a lung, a kidney, and a prostate.

* * * * *